(12) United States Patent
Arroyo et al.

(10) Patent No.: US 7,507,415 B2
(45) Date of Patent: Mar. 24, 2009

(54) WEST NILE VIRUS VACCINE

(75) Inventors: Juan Arroyo, Rockville, MD (US); Charles Miller, Lynn, MA (US); John Avram Catalan, Newton, MA (US); Thomas P. Monath, Harvard, MA (US)

(73) Assignee: Acambis Inc., Cambridge, MA (US)

( * ) Notice: Subject to any disclaimer, the term of this patent is extended or adjusted under 35 U.S.C. 154(b) by 404 days.

(21) Appl. No.: 10/715,868

(22) Filed: Nov. 17, 2003

(65) Prior Publication Data

US 2005/0053624 A1 Mar. 10, 2005
US 2007/0275015 A9 Nov. 29, 2007

Related U.S. Application Data

(63) Continuation-in-part of application No. PCT/US03/36623, filed on Nov. 13, 2003.

(60) Provisional application No. 60/426,592, filed on Nov. 15, 2002.

(51) Int. Cl.
*A61K 39/295* (2006.01)
*C12N 7/01* (2006.01)
*C12N 15/40* (2006.01)
*C12N 7/04* (2006.01)

(52) U.S. Cl. .................. 424/199.1; 435/235.1; 435/236; 424/218.1; 536/23.72

(58) Field of Classification Search .............. 424/218.1, 424/235.1, 202.1; 435/5, 235.1
See application file for complete search history.

(56) References Cited

U.S. PATENT DOCUMENTS

| 6,136,561 A | 10/2000 | Ivy et al. .................... 435/69.3 |
| 6,171,854 B1 | 1/2001 | Galler et al. |
| 6,184,024 B1 | 2/2001 | Lai et al. ................. 435/235.1 |
| 6,416,763 B1 | 7/2002 | McDonell et al. ........ 424/218.1 |
| 6,682,883 B1 * | 1/2004 | Monath et al. ................. 435/5 |
| 6,696,281 B1 * | 2/2004 | Chambers et al. ........ 435/235.1 |
| 6,962,708 B1 | 11/2005 | Chambers et al. |
| 2003/0044773 A1 | 3/2003 | Kleanthous et al. |
| 2003/0129201 A1 | 7/2003 | Monath et al. |
| 2003/0194801 A1 | 10/2003 | Bonaldo et al. |
| 2004/0223979 A1 | 11/2004 | Chambers et al. |
| 2004/0259224 A1 | 12/2004 | Guirakhoo |
| 2005/0002968 A1 | 1/2005 | Monath et al. |
| 2007/0184469 A1 | 8/2007 | Despres |

FOREIGN PATENT DOCUMENTS

| WO | WO 02/072835 | 9/1902 |
| WO | WO93/06214 | 4/1993 |
| WO | WO98/37911 | 9/1998 |
| WO | WO 01/39802 A1 | 6/2001 |
| WO | WO 02/102828 | 12/2002 |
| WO | WO 03/063725 A2 | 8/2003 |
| WO | WO 03/101397 | 12/2003 |
| WO | WO 03/103571 | 12/2003 |
| WO | WO 2004/045529 | 6/2004 |
| WO | WO 2005/040390 | 5/2005 |
| WO | WO 2005/049815 | 6/2005 |
| WO | WO 2005/082020 | 9/2005 |
| WO | WO 2006/044857 | 4/2006 |
| WO | WO 2006/116182 | 11/2006 |
| WO | WO 2007/051267 | 5/2007 |

OTHER PUBLICATIONS

Arroyo et al., ChimeriVax-West Nile Virus Live-Attenuated Vaccine: Preclinical Evaluation of Safety, Immunogenicity and Efficacy, 2004, Journal of Virology vol. 78, No. 22:12497-12507.*
Allison et al., Mutational Evidence for an Internal Fusion Peptide in Flavivirus Envelope Protein E, May 2001, vol. 75, No. 9:4268-4275.*
Poidinger et al., Molecular Characterization of the Japanese Encephalitis Serocomplex of the Flavivirus Genus, 1996, Virology 218:417-421.*
Yang et al., Induction of Potent Th1-Type Immune Responses from a Novel DNA Vaccine for West Nile Virus New York Isolate (WNV-NY1999), 2001, The Journal of Infectious Diseases 184:809-16.*
Guirakoo et al., "Immunogenicity, Genetic Stability, and Protective Efficacy of A Recombinant, Chimeric Yellow Fever-Japanese Encephalitis Virus (ChimerVax-JE) as a Live, Attenuated Vaccine Candidate Against Japanese Encephalitis," Virol. 257:363-372. 1999.*
Arroyo et al., "Molecular Basis for Attenuation of Neurovirulence of a Yellow Fever Virus/Japanese Encephalitis Virus Chimera Vaccine (ChimeriVax-JE)," J. Virol. 75:934-942, 2001.
Arroyo et al., "Yellow Fever Vector Live-Virus Vaccines: West Nile Virus Vaccine Development," Trends in Molecular Medicine 7:350-354, 2001.
Bray et al., "Construction of Intertypic Chimeric Dengue Viruses by Substitution of Structural Protein Genes," Proc. Natl. Acad. U.S.A. 88:10342-10346, 1991.
Caufour et al., "Construction, Characterization and Immunogenicity of Recombinant Yellow Fever 17D-Dengue Type 2 Viruses," Virus Research 1-14, 2001.
Chambers et al., "Mutagenesis of the Yellow Fever Virus NS2B/3 Cleavage Site: Determinants of Cleavage Site Specificity and Effects on Polyprotein Processing and Viral Replication," J. Virol. 69:1600-1605, 1995.
Chambers et al., "Vaccine Development Against Dengue and Japanese Encephalitis: Report of a World Health Organization Meeting," Vaccine 15:1494-1502, 1997.
Chambers et al., "Yellow Fever/Japanese Encephalitis Chimeric Viruses: Construction and Biological Properties," J. Virol. 73:3095-3101, 1999.
Coia et al., "Nucleotide and Complete Amino Acid Sequences of Kunjin Virus: Definitive Gene Order and Characteristics of the Virus-Specified Proteins," J. Gen. Virol. 69:1-21, 1988.

(Continued)

*Primary Examiner*—Mary E. Mosher
(74) *Attorney, Agent, or Firm*—Clark & Elbing LLP

(57) ABSTRACT

The invention provides chimeric flavivirus vaccines against West Nile virus and methods of using these vaccines to prevent or treat West Nile virus infection.

28 Claims, 1 Drawing Sheet

OTHER PUBLICATIONS

Davis et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," J. Virology 75:4040-4047, 2001.

Duarte dos Santos et al., "Complete Nucleotide Sequence of Yellow Fever Virus Vaccine Strains 17DD and 17D-213," Virus Research 35:35-41, 1995.

Galler et al., "Genetic Variability Among Yellow Fever Virus 17D Substrains," Vaccine 16:1-5, 1998.

Galler et al., "The Yellow Fever 17D Vaccine Virus: Molecular Basis of Viral Altenuation and its Use as an Expression Vector," Braz. J. Biol. Res. 30:157-168, 1997.

Guirakhoo et al., "Construction, Safety, and Immunogenicity in Nonhuman Primates of a Chimeric Yellow Fever-Dengue Virus Tetravalent Vaccine," J. Virol. 75:7290-7304, 2001.

Guirakhoo et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate Against Japanese Encephalitis," Virol. 257:363-372, 1999.

Lai et al., "Evaluation of Molecular Strategies to Develop a Live Dengue Vaccine," Clin. Diag. Virol. 10:173-179, 1998.

Mandl et al., "Sequence of the Genes Encoding the Structural Proteins of the Low-Virulence Tick-Borne Flaviviruses Langat TP21 and Yelantsev," Virol. 185:891-895, 1991.

Mandl et al., "Complete Genomic Sequence of Powassan Virus: Evaluation of Genetic Elements in Tick-Borne Versus Mosquito-Borne Flaviviruses," Virol. 194:173-184, 1993.

Marchevsky et al., "Phenotypic Analysis of Yellow Fever Virus Derived from Complementary DNA," American J. Tropical Medicine & Hygiene 52:75-80, 1995.

Monath et al., "Chemeric Yellow Fever Virus 17D-Japanese Encephalitis Virus Vaccine: Dose-Response Effectiveness and Extended Safety Testing in Rhesus Monkeys," J. Virol. 74:1742-1751, 2000.

Monath et al., "West Nile Virus Vaccine," Current Drug Targets-Infectious Disorders 1:1-14, 2001.

Pletnev et al., "Construction and Characterization of Chimeric Tick-Borne Encephalitis/Dengue Type 4 Viruses," Proc. Natl. Acad. Sci. U.S.A. 89:10532-10536, 1992.

Rice et al., "Transcription of Infectious Yellow Fever RNA from Full-Length cDNA Templates Produced by In Vitro Ligation," The New Biologist 1:285-296, 1989.

Shiu et al., "Genomic Sequence of the Structural Proteins of Louping III Virus: Comparative Analysis with Tick-Borne Encephalitis Virus," Virology 180:411-415, 1991.

Stocks et al., "Signal Peptidase Cleavage at the Flavivirus C-prM Junction: Dependence on the Viral NS2B-3 Protease for Efficient Processing Requires Determinants in C, the Signal Peptide, and prM," J. Virol. 72:2141-2149, 1998.

Van Der Most et al., "Chimeric Yellow Fever/Dengue Virus as a Candidate Dengue Vaccine: Quantitation of the Dengue Virus-Specific CD8 T-Cell Response," J. Virol. 74:8094-8101, 2000.

Venugopal et al., "Towards a New Generation of Flavivirus Vaccines," Vaccines 12:966-975, 1994.

Johnson et al., "Growth Characteristics of the Veterinary Vaccine Candidate ChimeriVax-West Nile (WN) Virus in Aedes and Culex Mosquitoes," Med. Vet. Entomol. 17:235-243, 2003.

Monath, "Prospects for Development of a Vaccine Against the West Nile Virus," Ann. NY Acad. Sci. 951:1-12, 2001.

Monath et al., "Clinical Proof of Principle for ChimeriVax: Recombinant Live, Attenuated Vaccines Against Flavivirus Infections," Vaccine 20:1004-1018, 2002.

Monath et al., "West Nile Virus Vaccine," Curr. Drug Targets Infect. Disord. 1:37-50, 2001.

Tesh et al., "Efficacy of Killed Virus Vaccine, Live Attenuated Chimeric Virus Vaccine, and Passive Immunization for Prevention of West Nile Virus Encephalitis in Hamster Model," Emerg. Infect. Dis. 8:1392-1397, 2002.

Supplementary European Search Report from Corresponding European Application No. EP 03 78 3570.

Allison et al., "Mapping of Functional Elements in the Stem-Anchor Region of Tick-Borne Encephalitis Virus Envelope Protein E," J. Virol. 73:5605-5612, 1999.

Allison et al., "Mutational Evidence for an Internal Fusion Peptide in Flavivirus Envelope Protein E," J. Virol. 75:4268-4275, 2001.

Lee et al., "Mechanism of Virulence Attenuation of Glycosaminoglycan-Binding Variants of Japanese Encephalitis Virus and Murray Valley Encephalitis Virus," 76:4901-4911, 2002.

Mandl et al., "Adaptation of Tick-Borne Encephalitis Virus to BHK-21 Cells Results in the Formation of Multiple Heparan Sulfate Binding Sites in the Envelope Protein and Attenuation In Vivo," J. Virol. 75:5627-5637, 2001.

Mandl et al., "Attenuation of Tick-Borne Encephalitis Virus by Structure-Based Site-Specific Mutagenesis of a Putative Flavivirus Receptor Binding Site," J. Virol. 74:9601-9609, 2000.

U.S. Appl. No. 08/807,445, filed Feb. 28, 1997, Chambers et al.

U.S. Appl. No. 09/007,664, filed Jan. 15, 1998, Chambers et al.

Bancroft, "Current Status of Dengue Vaccines and Prospects for the Future," *Puerto Rico Health Sci. J.* 6(1):23-26, 1987. Abstract only.

Barrett, "Current Status of Flavivirus Vaccines," *Ann. N. Y. Acad. Sci.* 951:262-271, 2001.

Bonaldo et al., "The Yellow Fever 17D Vaccine Virus as a Vector for the Expression of Foreign Proteins: Development of New Live Flavivirus Vaccines," *Mem. Inst. Oswaldo Cruz, Rio de Janeiro* 95(Suppl. 1):215-223, 2000.

Bonaldo et al., "Surface Expression of an Immundominant Malarie Protein B Cell Epitope by Yellow Fever Virus," *J. Mol. Biol.* 315:873-885, 2002.

Bonaldo et al., "Attenuation of Recombinant Yellow Fever 17D Viruses Expressing Foreign Protein Epitopes at the Surface," *J. Virology* 79:8602-8613, 2005.

Bonaldo et al., "Expression of Foreign Protein Epitopes at the Surface or Recombinant Yellow Fever 17D Viruses Based on Three-Dimensional Modeling of Its Envelope Protein," *Cell Biochem. Biophys.* 44:313-324, 2006.

Bray et al., "Genetic Determinants Responible for Acquisition of Dengue Type 2 Virus Mouse Neurovirulence," *J. Virology* 72:1647-1651, 1998.

Cardosa, "Dengue Vaccine Design: Issues and Challenges," *British Med. Bull.* 54(2):395-405, 1998.

Carle et al., "Experiments on the Transmission of an Icterogenic Agent in Yellow Fever Vaccine to Horses and Swine," *J. Bacteriol.* 48:45-69, 1944.

Chen et al., "Generation and Characterization of Organ-Tropism Mutants of Japanese Encephalitis Virus In Vivo and In Vitro, "*Virology* 223:79-88, 1996.

Dermime et al., "Vaccine and Antibody-Directed T Cell Tumour Immunotherapy," *Biochim. Biophys. Acta* 1704:11-35, 2004.

De Vries et al., "Genetic Manipulation of Equine Arteritis Virus Using Full-Length cDNA Clones: Separation of Overlapping Genes and Expression of a Foreign Epitope," *Virology* 270:84-97, 2000.

dos Santos et al., "Determinants in the Envelope E Protein and Viral RNA Helicase NS3 that Influence the Induction of Apoptosis in Response to Infection with Dengue Type 1 Virus," *Virology* 274:292-308, 2000.

Edelman et al., "Phase I Trial of 16 Formulation of a Tetravalent Live-Attenuated Dengue Vaccine," *Am. J. Trop. Med. Hyg.* 69(Suppl 6):48-60, 2003.

EZ::TN™ Insertion System(Epicentre). (May 29, 2001).

Goryshin and Reznikoff, "Tn5 In Vitro Transposition," J. Biol. Chem. 273:7367-7374, 1998.

Guirakhoo et al., "Recombinant Chimeric Yellow Fever-Dengue Type 2 Virus is Immunogenic and Protective in Nonhuman Primates,"*J. Virology* 74:5477-5485, 2000.

Guirakhoo et al., "Construction, Viremia, and Immunogenicity Profile of Recombinant Chimeric Yellow Fever/Dengue Viruses in Nonhuman Primates," Program and Abstracts of the 49th Annual Meeting of the American Society of Tropical Medicine and Hygiene, Houston, Texas, Oct. 29-Nov. 2, 2000, Supplement to *Am. J. Trop. Med. Hyg.*, 313, Abstract.

Guirakhoo et al., "Construction, Virenia, and Immunogencity Profile of Recombinant Chimeric Yellow Fever/Dengue Viruses in Nonhuman Primates," Program and Abstracts of the 49th Annual Meeting of the American Society of Tropical Medicine and Hygiene, Houston, Texas, Oct. 29-Nov. 2, 2000, Supplement to *Am. J. Trop. Med. Hyg.*, 1722, Abstract.

Guirakhoo et al., "Development of ChimeriVax™ -Yellow Fever Based Vaccines for Dengue and Japanese Encephalitis Viruses," 6th International Symposium on Positive Strand RNA Viruses, Paris, May 28-Jun. 2, 2001, Abstract.

Guirakhoo et al., "Viremia and Immunogenicity in Nonhuman Primates of a Tetravalent Yellow Fever-Dengue Chimeric Vaccine: Genetic Reconstuctions, Dose Adjustment, and Antibody Responses Against Wild-Type Dengue Virus Isolates,"*Virology* 298:146-159, 2002.

Guirakhoo et al., "Safety and Efficacy of Chimeric Yellow Fever-Dengue Virus Tetravalent Vaccine Formulations in Nonhuman Primates," *J. Virology* 78(9):4761-4775, 2004.

Guirakhoo et al., "A Single Amino Acid Substitution in the Envelope Protein of Chimeric Yellow Fever-Dengue 1 Vaccine Virus Reduces Neurovirulence for Suckling Mice and Viremia/Visceotropism for Monkeys," *J. Virology* 78(18):9998-10008, 2004.

Guirakhoo et al., "Live Attenuated Chimeric Yellow Fever Dengue Type 2 (ChimeriVax™ -DEN2) Vaccine: Phase I Clinical Trial for Safety and Immunogenicity," *Human Vaccines* 2(2):60-67, 2006.

Guy et al., "Evaluation by Flow Cytometry of Antibody-Dependent Enhancement (ADE) of Dengue Infection by Sera from Thai Children Immunized with a Live-Attenuated Tetravalent Dengue Vaccine," *Vaccine* 22:3563-3574, 2004.

Halstead and Deen, "Rapid Review: The Future of Dengue Vaccines," *The Lancet* 360:1243-1245, 2002.

Hurrelbrink and McMinn, "Attenuation of Murray Valley Encephalitis Virus by Site-Directed Mutagenesis of the Hinge and Putative Receptor-Binding Regions of the Envelope Protein," *J. Virology* 75:7692-7702, 2001.

Innis and Eckels, "Progress in Development of Live-Attenuated, Tetravalent Dengue Virus Vaccine by the United States Army Medical Research and Material Command," *Am. J. Trop. Med. Hyg.* 69(Suppl 6):1-4, 2003.

Kanesa-thasan et al., "Safety and Immunogenicity of Attenuated Dengue Virus Vaccines (Aventis Pasteur) in Human Volunteers," *Vaccine* 19:3179-3188, 2001.

Kolaskar and Kulkrani-Kale, "Prediction of Three-Dimensional Structure and Mapping of Conformational Epitopes of Envelope Glycoprotein of Japanese Encephalitis Virus," *Virology* 261:31-42, 1999.

Kurane et al., "Immunity and Immunopathology in Dengue Virus Infections," *Sem. Immunol.* 4(2):121-127, 1992. Abstract only.

Lai and Monath, "Chimeric Flaviviruses: Novel Vaccines Against Dengue Fever, Tick-Borne Encephalitis, and Japanese Encephalitis," *Adv. Virus Res.* 61:469-509, 2003.

Laoprasopwattana et al., "Dengue Virus (DV) Enhancing Antibody Activity In Preillness Plasma does not Predict Subsequent Disease Severity or Viremia in Secondary DV Infection," *J. Infect. Dis.* 192:510-519, 2005. Erratum in *J. Infect. Dis.* 192:1863, 2005.

Lee et al., "Changes in the Dengue Virus Major Envelope Protein on Passaging and Their Localization on the Three-Dimensional Structure of the Protein," *Virology* 232:281-290, 1997.

Li et al., "Chimeric Influenza Virus Induces Neutralizing Antibodies and Cytotoxic T Cells Against Human Immunodeficiency Virus Type 1," *J. Virology* 67(11):6659-6666, 1993.

McAllister et al., "Recombinant Yellow Fever Viruses are Effective Therapeutic Vaccines for Treatment of Murine Experimental Solid Tumors and Pulmonary Metastases," *J. Virology* 74(19):9197-9205, 2000.

McMinn, "The Molecular Basis of Virulence of the Encephalitogenic Flaviviruses," *J. Gen. Virology* 78:2711-2722, 1997.

Modis et al., "A Ligand-Binding Pocket in the Dengue Virus Envelope Glycoprotein," *Proc. Natl. Acad. Sci. U.S.A.* 100(12):6986-6991, 2003.

Monath et al., "Recombinant, Chimaeric Live, Attenuated Vaccine (ChimerVax™) Incorporating the Envelope Genes of Japanese Encephalitis (SA14-14-2) Virus and the Capsid and Nonstructural Genes of Yellow Fever (17D) Virus is Safe, Immunogenic and Protective in Non-Human Primates," *Vaccine* 17:1869-1882, 1999.

Monath, "Molecular Distinctions Between Attenuated (Vaccine) and Virulent Yellow Fever Viruses," In, Plotkin SA and Orenstein WA (eds.), Vaccines, 3rd edition, Saunders (Philadelphia), pp. 815-879, 1999.

Monath et al., "Yellow Fever 17D as a Vector for Vaccines Against Heterologous Flaviviruses," American Society for Virology, 19th Annual Meeting, Colorado State University, Fort Collins, Colorado, Jul. 8-12, 2000, Abstract W17-7, p. 85.

Monath, "Yellow Fever: an Update," *Lancet Infect. Dis.* 1:11-20, 2001.

Monath et al., "Single Mutation in the Flavivirus Envelope Protein Hinge Region Increases Neurovirulence for Mice and Monkeys but Decreases Viscertropism for Monkeys: Relevance to Development and Safety Testing of Live, Attenuated Vaccines," *J. Virology* 76:1932-1943, 2002.

Morens and Halstead, "Measurement of Antibody-Dependent Infection Enhancement of Four Dengue Virus Serotypes by Monoclonal and Polyclonal Antibodies," *J. Gen. Virol.* 71(12):2909-2914, 1990.

Pervikov, "Development of Dengue Vaccine," W.H.O. Dengue Bulletin 24, 2000.

Rey et al., "The Envelope Glycoprotein From Tick-Borne Encephalitis Virus at 2A Resolution," *Nature* 375:291-298, 1995.

Rey, "Dengue Virus Envelope Glycoprotein Structure: New Insight Into Its Interactions During Viral Entry," *Proc. Natl. Acad. Sci. U.S.A.* 100(12):6899-6901, 2003.

Rothman, "Dengue: Defining Protective Versus Pathologic Immunity," *J. Clin. Invest.* 113(7):946-951, 2004.

Ryman et al., "Yellow Fever Virus Envelope Protein has Two Discrete Type-Specific Neutralizing Epitopes," *J. Gen. Virology* 78:1353-1356, 1997.

Sabchareon et al., "Safety and Immunogenicity of Tetravalent Live-Attenuated Dengue Vaccines in Thai Adult Volunteers: Role of Serotype Concentration, Ratio, and Multiple Doses," *Am. J. Trop. Med. Hyg.* 66:264-272, 2002.

Stephenson, "Flavivirus Vaccines," *Vaccine* 6(6):471-480, 1988. Abstract only.

Sun et al., "Vaccination of Human Volunteers with Monvalent and Tetravalent Live-Attenuated Dengue Vaccine Candidates," *Am. J. Trop. Med. Hyg.* 69(Suppl 6):24-31, 2003.

Theiler and Smith, "The Use of Yellow Fever Virus Modified by In Vitro Cultivation for Human Immunization," *Rev. Med. Virol.* 10:3-16, 2000.

Vlaycheva et al., "Yellow Fever 17D Virus: Pseudo-Revertant Suppression of Defective Virus Penetration and Spread by Mutations in Domains II and III of the E protein," *Virology* 327:41-49, 2004.

Volk et al., "Solution Structure and Antibody Binding Studies of the Envelope Protein Domain III from the New York Strain of West Nile Virus," *J. Biol. Chem.* 279:38755-38761, 2004.

Wang et al., "Comparison of the Genomes of the Wild-Type French Viscerotropic Strain of Yellow Fever Virus with its Vaccine Derivative French Neurotropic Vaccine," *J. Gen. Virology* 76:2749-2755, 1995.

Yamshchikov et al., "An Attenuated West Nile Prototype Virus is Highly Immunogenic and Protects Against the Deadly NY99 Strain: A Candidate for Live WN Vaccine Development," *Virology*, 330:304-312, 2004.

International Search Report from WO02//102828 dated Apr. 18, 2003.

International Search Report from WO03/063725 dated Jun. 25, 2003.

International Search Report from WO03/101397 dated Sep. 4, 2003.

International Search Report from WO03/103571 dated Dec. 12, 2003.

International Search Report from WO04/045529 dated Jun. 28, 2004.

International Search Report from WO05/082020 dated Sep. 30, 2005.

International Search Report from WO06/044857 dated May 30, 2006.

International Search Report from WO06/116182 dated Jul. 17, 2006.

European Search Report from European Application No. 05012770. (Dec. 13, 2005).

Johnson et al., "Growth Characteristics of the Veterinary Vaccine Candidate ChimeriVax-West Nile (WN) Virus in Aedes and Culex Mosquitoes," Med. Vet. Entomal. 17:235-243, 2003.

Monath, "Prospects for Development of a Vaccine Against the West Nile Virus," Ann. NY Acad. Sci. 951:1-12, 2001.

Monath et al., "Clinical Proof of Principle for ChimenVax: Recombinant Live, Attenuated Vaccines Against Flavivirus Infections," Vaccine 20:1004-1018, 2002.

Monath et al., "West Nile Virus Vaccine," Curr. Drug Targets Infect. Discord. 1:37-50, 2001.

Tesh et al., "Efficacy of Killed Virus Vaccine, Live Attenuated Chimeric Virus Vaccine, and Passive Immunization for Prevention of West Nile Virus Encephalitis in Hamster Model," Emerg. Infect. Dis. 8:1392-1397, 2002.

Supplementary European Search Report from Corresponding European Application No. EP 03 78 3570. Date not available.

European Office Action, European Patent Application No. 03 783 570.9-2405, dated Aug. 27, 2008.

Reply to European Office Action, European Patent Application No. 03 783 570.9-2405, dated Mar. 4, 2008.

* cited by examiner

Figure 1. Reciprocal neutralizing antibody titer (PRNT$_{50}$) results from ICR mice vaccinated with YF/WN *wt* or YF/WN$_{FVR}$

SEQUENCE LISTING

<160> NUMBER OF SEQ ID NOS: 7

<210> SEQ ID NO 1
<211> LENGTH: 46
<212> TYPE: DNA
<213> ORGANISM: Artificial Sequence
<220> FEATURE:
<223> OTHER INFORMATION: Primer

<400> SEQUENCE: 1
caacggctgc ggatttttg gcaaaggatc cattgacaca tgcgcc        46

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
gaaagagaat attaagtaca aagtggccat ttttgtcc               38

<210> SEQ ID NO 3
<211> LENGTH: 50
<212> TYPE: DNA
<213> ORGANISM: Artificial Sequence
<220> FEATURE:
<223> OTHER INFORMATION: Primer

<400> SEQUENCE: 3
gccctcgagc ggccgattca gcatcactcc tgctgcgcct tcagtcacac    50

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gccctcgagc ggccgattca gcatcac                           27

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
gcaacactgt catgttaacg tcgggtcatt tg                     32

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
cttgggactc ccgtggacac cggtcacggc ac                     32

```
<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7 gggtgttca ctagtgttgg gcgggctgtc catcaagtg                                      39
```

WEST NILE VIRUS VACCINE

CROSS-REFERENCE TO RELATED APPLICATIONS

This application claims priority from U.S. Ser. No. 60/426,592, filed Nov. 15, 2002, which is incorporated by reference herein in its entirety. This application also is a continuation-in-part of PCT international application PCT/US03/36623, filed Nov. 13, 2003 (WO 2004/045529, published Jun. 3, 2004).

STATEMENT AS TO FEDERALLY FUNDED RESEARCH

This invention was made with government support under grant number 5R01AI048297-03 awarded by the National Institute of Allergy and Infectious Diseases (NIAID). The government has certain rights in the invention.

FIELD OF THE INVENTION

This invention relates to vaccines against West Nile virus.

BACKGROUND OF THE INVENTION

Since its earliest detection in the northern hemisphere, West Nile (WN) virus has continued to spread rapidly across North America. The first cases were diagnosed in the New York area in 1999, and by 2002 human mortality increased to over 150 cases and the virus spread has continued, reaching as far as California. The appearance of infected/dead birds indicates that there is a large pool of infected mosquitoes in the geographical areas of incidence. To date, there is no effective drug treatment against West Nile virus and methods of surveillance and prevention are not significantly impacting the number of cases of human infection. Thus, the risks of the virus migrating into the southern American continent, as well as an epidemic in underdeveloped countries, are extremely high.

West Nile virus is a member of the flavivirus family. These viruses are small, enveloped, positive-strand RNA viruses that are of concern in many medical and veterinary settings throughout the world. Examples of flaviviruses in addition to West Nile virus include Yellow Fever virus, Japanese Encephalitis virus, and Dengue viruses.

Flavivirus proteins are produced by translation of a single, long open reading frame to generate a polyprotein, which undergoes a complex series of post-translational proteolytic cleavages by a combination of host and viral proteases to generate mature viral proteins (Amberg et al., J. Virol. 73:8083–8094, 1999; Rice, "Flaviviridae," In *Virology*, Fields (ed.), Raven-Lippincott, New York, 1995, Volume I, p. 937). The virus structural proteins are arranged in the polyprotein in the order C-prM-E, where "C" is capsid, "prM" (or "pre-membrane") is a precursor of the viral envelope-bound M (membrane) protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein.

SUMMARY OF THE INVENTION

The invention provides nucleic acid molecules that include sequences encoding the pre-membrane and envelope proteins of West Nile virus and the capsid and non-structural proteins of Yellow Fever virus. The West Nile virus pre-membrane or envelope proteins of these chimeras include one or more attenuating mutations, which can be, for example, an amino acid substitution at positions 107, 316, and/or 440 of the envelope protein. As specific examples, the amino acid substitution at position 107 can be leucine to phenylalanine (or a conservative amino acid thereof); the amino acid substitution at position 316 can be alanine to valine (or a conservative amino acid thereof); and the amino acid substitution at position 440 can be lysine to arginine (or a conservative amino acid thereof).

The invention also includes chimeric flaviviruses encoded by the nucleic acid molecules described herein, as well as methods of inducing an immune response to West Nile virus in a subject by administration of such chimeric flaviviruses. Further, the invention includes the use of such chimeric flaviviruses in vaccination methods and their use in methods for preparing medicaments for use in such methods. The methods described herein can be carried out with subjects that are at risk of developing, but do not have, West Nile virus infection, as well as with subjects that are infected with West Nile virus. The invention also provides methods of making the chimeric flaviviruses described herein.

The invention provides several advantages. For example, as is discussed in more detail below, the attenuating mutations of the viruses of the invention result in decreased neurovirulence, yet do not adversely impact the ability of the viruses to induce an effective immune response. Thus, the viruses of the invention provide an effective and safe approach to preventing and treating West Nile virus infection.

Other features and advantages of the invention will be apparent from the following detailed description and the claims.

BRIEF DESCRIPTION OF THE DRAWING

FIG. 1 is a graph showing reciprocal neutralizing antibody titer ($PRNT_{50}$) results from ICR mice vaccinated with YF/WN wt or $YF/WN_{FVR}$. Individual neutralizing antibody titers against YF/WN wt virus are shown. White symbols denote mice that did not survive IP challenge with WNV NY-99 strain. 100% survival was obtained in groups vaccinated with $10^3$ pfu dose of YF/WN wt and with $10^5$ pfu dose of $YF/WN_{FVR}$. Only 40% mice survived challenge in the group vaccinated with $10^3$ pfu of $YF/WN_{FVR}$.

DETAILED DESCRIPTION

The invention provides vaccines and methods for use in preventing and treating West Nile (WN) virus infection. The methods of the invention involve vaccination of subjects with a live, attenuated chimeric flavivirus that consists of a Yellow Fever virus in which the pre-membrane and envelope proteins have been replaced with those of West Nile virus. The West Nile virus proteins of the chimeras of the invention include one or more attenuating mutations, as is described further below.

General methods for constructing and administering chimeric flaviviruses that can be used in the present invention are described in detail, for example, in U.S. patent application Ser. Nos. 09/007,664, 09/121,578 (issued as U.S. Pat. No. 6,962,708), and Ser. No. 09/452,638 issued as U.S. Pat. No. 6,696,281); International applications PCT/US98/03894 (WO 98/37911) and PCT/US00/32821 (WO 01/39802); and Chambers et al., J. Virol. 73:3095–3101, 1999, which are each incorporated by reference herein in their entirety. As is discussed further below, these methods are modified for use in the present invention by including a step of introducing one or more attenuating mutations into inserted West Nile virus sequences. Methods that can be used for producing viruses in the invention are also described in PCT/US03/01319 (WO 03/060088 A2), which is also incorporated herein by reference.

In one example of a chimeric virus of the invention, the attenuating mutation is in the region of position 107, 316, or 440 (or a combination thereof) of the West Nile virus envelope protein. The mutations can thus be, for example, in one or more of amino acids 102–112, 311–321, and/or 435–445 of the West Nile envelope protein. As a specific example, using the sequence of West Nile virus strain NY99-flamingo 382–99 (GenBank Accession Number AF196835; SEQ ID NOs:8 (nucleic acid) and 9 (amino acid)) as a reference, lysine at position 107 can be replaced with phenylalanine, alanine at position 316 can be replaced with valine, and/or lysine at position 440 can be replaced with arginine. In addition to the amino acids noted above, the substitutions can be made with other amino acids, such as amino acids that would result in a conservative change from those noted above. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine. In a specific example, a chimera of the invention includes each of the specific substitutions noted above. Further, as is discussed further below, additional residues (e.g., positions 138, 176, and/or 280) can also be altered in the chimeric viruses of the present invention.

The vaccines of the invention can be administered in amounts and by using methods that can readily be determined by persons of ordinary skill in this art. The vaccines can be administered and formulated, for example, as a fluid harvested from cell cultures infected with the chimeric virus. The live, attenuated chimeric virus can be formulated as a sterile aqueous solution containing between $10^2$ and $10^8$, e.g., between $10^6$ and $10^7$, infectious units (e.g., plaque-forming units (pfu) or tissue culture infectious doses) in a dose volume of 0.1 to 1.0 ml, to be administered by, for example, subcutaneous, intramuscular, or intradermal routes. In addition, a mucosal route, such as the oral route, can be selected. Selection of an appropriate amount of chimera to administer can be determined by those of skill in this art, and this amount can vary due to numerous factors, e.g., the size and general health of the subject to whom the chimera is to be administered. The subject can be vaccinated a single time or, if necessary, follow-up immunization can take place.

As is noted above, the vaccines can be administered as primary prophylactic agents to a subject that is at risk of West Nile virus infection. The vaccines can also be used as secondary agents for treating West Nile virus-infected subjects by stimulating an immune response against the infecting virus. Also, although not required, adjuvants can be used to enhance the immunogenicity of the chimeric West Nile virus vaccines. Selection of appropriate adjuvants can readily be carried out by those of skill in this art.

The invention is based, in part, on the following experimental results.

Experimental Results

To increase the safety profile of a West Nile/Yellow Fever chimeric vaccine, we investigated whether attenuating point mutations in the envelope protein would reduce neurovirulence. As is described in detail below, we constructed a YF/WN chimera that lacks the mouse neuroinvasiveness of West Nile virus and is less neurovirulent than the Yellow Fever vaccine strain YF 17D in both mice and monkey models. The following is a description of the envelope protein mutagenesis, and an assessment of safety, immunogenicity, and efficacy of this and related viruses in mouse and rhesus models.

Materials and Methods

YF/WN Chimeric Constructs and Molecular Procedures

Chimeric flaviviruses are constructed using the ChimeriVax™ technology, which involves using a two-plasmid system that was previously described (see, e.g., U.S. patent application Ser. Nos. 09/007,664, 09/121,587, (issued as U.S. Pat. No. 6,962,708), and Ser. No. 09/452,638 (issued as U.S. Pat. No. 6,696,281); International applications PCT/US98/03894 (WO 98/37911) and PCT/US00/32821 (WO 01/39802); and Chambers et al., J. Virol. 73:3095–3101, 1999). The two-plasmid system provides plasmid stability in *E. coli* and a suitable method to manipulate the cloned yellow fever (YF) backbone, facilitating replacement of the YF prM and E genes with those of a flavivirus target. The West Nile (WN) virus prM and E genes used were cloned from WNV flamingo isolate 383–99, sequence GenBank accession number AF196835. Virus prME cDNA was obtained by RT-PCR (XL-PCR Kit, Perkin Elmer). The 5' end of WN prM gene was cloned precisely at the 3' end of the YF 17D capsid gene by overlap-extension PCR using Pwo polymerase (Roche). This cloning step maintains the integrity of the cleavage/processing signal encoded at the 3' end of the YF capsid gene. The 3' end of the E gene was also cloned precisely at the 5' end of the YF NS1 coding sequence by overlap-extension PCR. Use of this two-plasmid system in the cloning of the prME region of West Nile virus into the YF 17D backbone was described previously (Arroyo et al., Trends in Molecular Medicine 7(8): 350–354, 2001). Silent mutations were introduced into the sequence of prM and E to create unique restriction sites Bsp EI and Eag I. Digestion of the two plasmids with these enzymes generated DNA fragments that were gel purified and ligated in vitro to produce a full-length chimeric cDNA. The cDNA was linearized with Xho I to facilitate in vitro transcription by SP6 polymerase (Epicentre). The RNA product was introduced into eukaryotic cell lines permissive for viral RNA translation and replication of the virus.

Point mutations were introduced at various E gene codons to produce variants of the original chimera coding for wild-type WN prME. Table 1 shows the mutation target sites and the oligonucleotide sequences used to create the YF/WN chimeras described below. Site mutations were confirmed by sequencing of the envelope proteins (prME region) of the resulting viruses. Virus cDNA templates for sequencing originated from RNA extracted from virus supernatants (Trizol LS, Invitrogen), followed by RT-PCR (XL-PCR Kit, Perkin Elmer) and sequencing with the use of synthetic primers (Invitrogen) and a CEQ 2000 sequencer (Beckman).

Viruses and Cell Lines

Chimeric YF/WN (i.e., ChimeriVax™-West Nile) viruses were prepared by RNA transfection (passage 1 virus, P1) into a Vero E6 cell line (ATCC, CIDVR UMASS Medical Center Worcester, Mass.). Research master seeds (RMS) were prepared by additional amplifications (either passage 2 or 3 at a 0.001 MOI) in Vero E6 cells. Vero E6 cells were maintained in MEM (Invitrogen), 10% FBS (Hyclone). Preparation of preMaster Seeds (PMS) for manufacture of the vaccine was initiated by RNA transfection into a serum free Vero (SF-Vero) cell line (ATCC, Baxter/Immuno Orth, Austria), followed by an amplification passage in the same SF-Vero cell line to produce a P2 PMS or preMaster Seed. The SF-Vero cell line was propagated and maintained in a serum free, protein free media formulation VT-Media (Baxter/Immuno, Austria). The wild type WN virus used was a NY-99 strain (NY99-35262-11 flamingo isolate) obtained from CDC, Fort Collins, Colo. (CDC stock designation B82332W) with two additional passages in Vero E6 cells to produce a Master Virus Bank. YF 17D is a commercial vaccine (YF-VAX®, Aventis Pasteur, Swiftwater, Pa.) used here after reconstitution of the lyophilized product or after one passage in Vero E6 cells (ATCC, Acambis Inc., Cambridge, Mass.).

Mouse Neuroinvasiveness and Neurovirulence in Adult and Suckling Mice; Immunogenicity and Challenge Titer Detection Methods (Inoculation Procedure, Plague Assay, PRNT)

Mice were inoculated intraperitoneally (IP) for neuroinvasion tests or during challenge with wild type WN virus. IP inoculation volumes were 100–200 µl administered with a 25G syringe. Adult and suckling mice were inoculated intracerebrally (IC) for neurovirulence testing. An inoculation volume of 20 µl administered on the right side of the frontal lobe of the brain was used for IC administration. Viruses were diluted in M199 with HEPES buffer (Invitrogen) and 20% FBS (Hyclone) unless otherwise indicated. Plaque assays in Vero cells were carried out to verify the titer of virus inoculi (Monath et al., J. Virol. 74(4):1742–1751, 2000).

Mice were observed for a period of 21 days to determine neuroinvasion, neurovirulence, or survival after West Nile virus challenge. Morbidity and mortality were observed/scored and survivors were euthanized.

To determine neutralizing antibody titers, mice were bled by the retroorbital route and serum was separated by centrifugation. Plaque reduction neutralization assays (PRNT) were used to measure titers of neutralizing antibody in serum.

Rhesus Neurovirulence Study

The test in rhesus monkeys to determine the neurovirulence of yellow fever (YF) vaccines, as described in WHO guidelines, was used to determine safety of YF/WN chimeras (Monath et al., J. Virol. 74(4):1742–1751, 2000). Animals were inoculated IC, and blood samples were obtained daily to measure viremia levels using the plaque assay technique. Animals were observed daily for signs of disease-associated symptoms, such as fever or tremors. Animals were euthanized 30 days after infection and brain and spinal chord tissues were then removed for histopathology. Neuropathology was scored following the WHO defined system and the values were analyzed for pathology relative to those of the YF 17D vaccine standard.

Rhesus Immunogenicity and Challenge

Rhesus monkeys were vaccinated by subcutaneous administration of a single 0.5 ml dose of vaccine containing a nominal 4 log10 PFU. Viremia was measured by plaque assays of the diluted serum on Vero cells using serum samples collected daily between days 0 to 10 (Monath et al., J. Virol. 74(4):1742–1751, 2000). Neutralizing antibody levels were measured by plaque reduction neutralization titer assays (PRNT) (Monath et al., J. Virol. 74(4):1742–1751, 2000). Animals were challenged 64 days post vaccination with wild-type WN virus NY99.

Genetic Stability (in vivo and in vitro Passage) and Sequencing

A YF/WN wt (i.e., ChimeriVax™-WN$_{01}$) construct without attenuating mutations in the E protein was passed six times in Vero E6 cells followed by six passages in suckling mice by the IC route. YF/WN$_{FVR}$ (i.e., ChimeriVax™-WN$_{02}$) preMaster Seed and Research Master Seed constructs with 3 attenuating mutations introduced in the E protein were passed 12 and 10 times, respectively, in serum free, protein free SF-Vero cell substrate. All passages were performed with an initial 0.01 MOI followed by harvest on the third day and continuing without titration to determine virus potency. Virus titers used at each passage were later calculated by plaque assay. Neurovirulence of the passaged viruses was measured by adult or suckling mice inoculations IC. Viral RNA was then sequenced.

Results

Virulence Phenotype of YF/WN wt Relative to YF 17D (YF-VAX®)

The initial West Nile virus chimera encoded the envelope and premembrane protein genes of the WN NY99 wild type strain (i.e., YF/WN wt or ChimeriVax™-WN$_{01}$). This chimeric virus lacked the ability to cause encephalitis after IP inoculation at doses of $10^6$ pfu in the ICR mouse (Table 2). Encephalitis was assessed by daily observation of changes in motor behavior, leading to paralysis and death. The YF/WN wt lack of neuroinvasion in the adult mouse was also observed in mice inoculated with the YF 17D vaccine by others (Ryman et al., Virology 230(2):376–380, 1997). In contrast, the WN NY99 wild type virus was lethal for mice when inoculated by the IP route with as little as 1–4 pfu (Beasley et al., Virology 296:17–23, 2002). The IC $LD_{50}$ of YF/WN wt was estimated here to be between $10^3$ and $10^5$ pfu. The neurovirulence phenotype of YF/WN wt is lower than that of YF 17D virus, where the ICR mice IC $LD_{50}$ is between $10^1$ and $10^2$ pfu. However, the YF/WN wt virus did not show a clear endpoint in the 21 day old mouse (Table 3).

Multi-site Mutagenesis Approaches

Amino acids in the envelope protein were changed to determine whether these changes would reduce the virulence of YF/WN chimeras. Changes in virulence were evaluated in the mouse model and compared to the neurovirulence of the original chimera YF/WN wt. Amino acid residues mapping to the YF/WN wt envelope (E) gene positions 107, 138, 176, and 280 were all mutated in a singular construct to encode amino acid residues F, K, V, and M, respectively. The new chimeric virus was identified as YF/WN$_{FKVM}$. Chimeras were then constructed in which each amino acid residue in the FKVM group was singly mutated to assess its individual role in neurovirulence (Table 4). In addition, mutations at amino acid residues 316 and 440 were mutated to V and R, respectively, based on previous data indicating that mutations in the E protein which mapped to these regions may function in the biology of the E protein third domain (Rey et al., Nature 375(6529): 291–298, 1995; Allison et al., J. Virol. 75(9): 4268–4275, 2001). Our observations of the neurovirulence of chimeras having modified amino acids in the E protein indicated that residues 107, 316, and 440 are the most important amino acids contributing to neurovirulence of WN virus. Based on this information, a multi-site YF/WN$_{FVR}$ construct was built and selected as our vaccine candidate. All multi-site chimeras grew to titers of $10^7$ pfu/mL in serum free SF Vero cells.

Neurovirulence Studies in Mice and Rhesus Monkeys

Mouse neurovirulence of viruses with single or multi-site mutations in the envelope protein gene of YF/WN wt was measured in 21 day old mice inoculated by the IC route with virus doses between $10^4$ and $10^5$ pfu. This assessment identified residues 107 and 280 (Table 4) and the combination of 316/440 (Table 5) as the more dominant attenuating mutations as measured by mouse mortality and relative average survival time (AST). The chimera selected as our vaccine candidate that had a combination of mutations F, V, and R at residues 107, 316, and 440, respectively, was avirulent in the adult mouse (Table 6). However, some neurovirulence was observed in two day old suckling mice, similar to the ChimeriVax™-JE vaccine that is safe for humans (Monath et al., Vaccine 20:1004–1018, 2002).

The rhesus monkey neurovirulence phenotype of the West Nile chimeras was measured with the YF/WN wt construct and compared to that of the YF 17D vaccine. Rhesus monkeys were inoculated by the IC route with YF/WN wt and compared to YF 17D vaccine inoculates. The chimera induced viremia titers and duration similar to the YF 17D vaccine. This virus was not more neurovirulent than the YF vaccine, indicating that the YF/WN chimeras are as safe as the YF 17D vaccine.

Immunogenicity Studies in Mice and Rhesus Monkeys

We compared the immunogenicity of the YF/WN wt chimera and the YF/WN$_{FVR}$ construct, which has mutations at envelope residues 107, 316, and 440. Mice were inoculated by the subcutaneous (SC) route with vaccine doses ranging between 2 to 5 log$_{10}$ pfu. Serum was collected four weeks after immunization and titrated for neutralizing antibodies. The data in FIG. 1 show that site-targeted attenuation of the YF/WN wt construct resulted in a less immunogenic virus. Intraperitoneal challenge of the immunized mice with wild type WN NY99 virus revealed a vaccine potency-to-efficacy correlation with the constructs. All of the mice immunized with a 10$^5$ pfu/ml dose of either of the YF/WN chimeras were protected from virulent virus challenge.

In rhesus monkeys, the immunogenicity of vaccine candidates with one, two, or three attenuating mutations, YF/WN$_{107}$F, YF/WN, $_{316}$V$_{440}$R, or YF/WN$_{FVR}$ were equal. There were no significant differences in the respective antibody titers when the animals received a 10$^4$ pfu vaccine dose. Efficacy studies determined by post immunization challenge with wild type WN NY99 virus clearly showed in the WN vaccine candidates tested in the rhesus model were 100% efficacious relative to control animals (Table 7).

Post-vaccination viremia in rhesus macaques was of similar duration relative to that induced by the YF 17D vaccine, but lower in magnitude, with a linear correlation to the number of attenuating unique mutations in the chimeras (Table 8). Nevertheless, assessment of safety based on viscerotropism (or post vaccination viremia) shows that any one of the vaccine candidates tested in the macaque model is safer than YF 17D.

Post IC challenge of the immunized rhesus macaques with 5.38 log$_{10}$ pfu of WN NY99 did not produce detectable viremia, and no clinical signs of disease or mortality were observed in animals vaccinated with YF/WN constructs. Significant viremia due to WNV replication was detected in the YF 17D vaccinees. Viremia levels detected in animals in this group had a mean log$_{10}$ pfu titer of 2.25±0.62, with a mean duration of 3.5 days. These viremia levels are similar to those observed in the non-vaccinated control group (n=2), with a mean log$_{10}$ pfu titer of 2.33±0.47 and 4.5 days mean duration. Two out of four rhesus macaques vaccinated with YF 17D survived IC challenge with WN NY99 strain. The survivors lost appetite and showed symptoms of lethargy with elevated temperatures post challenge. Animals that were euthanized post WNV NY99 strain challenge presented symptoms including fever and tremors.

Genetic Stability

In vitro and in vivo substrate-passage studies with YF/WN wt or YF/WN$_{FVR}$ chimeras were conducted to determine genetic stability of the constructs when grown in stationary cultures. After six in vitro Vero E6 cell passages, followed by six in vivo ICR adult mouse brain passages of YF/WN wt, we found no undesirable mutations in the envelope gene (prM, E) region of this chimera. A heterozygous mutation in the E protein at position E336, resulting in a cysteine to serine, was identified after ten in vitro passages of the YF/WN$_{FVR}$ virus in Vero E6 cells. In a separate study, in vitro passage of YF/WN-$_{FVR}$ SF-Vero cells resulted in selection of a mutation at position E 313, which changed the amino acid at this position from glycine to arginine. During all of the serial passages of the virus in Vero cells, no reversions/mutations were detected at target residues 107F, 316V, or 440R, which are involved in virus neurovirulence.

TABLE 1

Switch Oligonucleotides used for site-mutagenesis

| E Protein position and residue | Primer | Marker Site |
|---|---|---|
| 107 L F | 5' CAACggCTgCggATTTTTTggCAAAggATCCATTgACACATgCgCC 3' | Bam HI |
| 138 E K | 5' gAAAgAgAATATTAAgTACAAAgTggCCATTTTTgTCC 3' | Ssp I |
| *176 V | 5' gCCCTCgAgCggCCgATTCAgCATCACTCCTgCTgCgCCTTCAgTCACAC 3' | |
| *176 Y | 5' gCCCTCgAgCggCCgATTCAgCATCAC-3' | |
| 280 K M | 5'-gCAACACTgTCATgTTAACgTCgggTCATTTg 3' | Hpa I |
| 316 A V | 5'-CTTgggACTCCCgTggACACCggTCACggCAC-3' | Age I |
| 440 K R | 5'-ggggTgTTCACTAgTgTTgggCgggCTgTCCATCAgTg-3' | Spe I |

Primers for site-directed mutagenesis to create mutant attenuated Yellow Fever/West Nile Virus. Nucleotide changes that introduce a new amino acid are indicated in bold. Silent restriction sites introduced are underlined. Primers indicated with an * (asterisk) are cloning primers used to sub-clone the fragment. One incorporates a nucleotide change while the other does not.

TABLE 2

Neuroinvasiveness of YF/WN wt (ChimeriVax ™-West Nile 01) relative to YF 17D, dose response in ICR mice[1]

| Virus IP | Dose ($log_{10}$ PFU) | % Mortality (no. dead/no. tested) | AST[2] |
|---|---|---|---|
| YF/WN wt | 0.89 | 0 (0/5) | — |
| (P2) | 2.23 | 0 (0/5) | — |
|  | 3.24 | 0 (0/5) | — |
|  | 4.06 | 0 (0/5) | — |
|  | 5.45 | 0 (0/5) | — |
|  | 6.51 | 0 (0/5) | — |
| YF17D | 2.78 | 0 (0/3) | — |
| (ATCC) | 4.48 | 0 (0/3) | — |
| Sham | N/A | 0 (0/3) | — |

[1]Harlan-Sprague ICR strain 3–4 weeks old female mice were used.
[2]AST = Average Survival Time.
YF/WN wt P2 indicates a second-generation passage virus on Vero cells.
West Nile virus strains are typically neuroinvasive after IP inoculation.

TABLE 3

Neurovirulence of YF/WN wt (ChimeriVax ™-West Nile 01) relative to YF 17D, dose response (Harlan-Sprague ICR strain 3–4 weeks old female mice)

| Virus IC | Dose[1] ($log_{10}$ PFU) | % Mortality (no. dead/no. tested) | AST |
|---|---|---|---|
| YF/WN wt | −2 | 0 (0/5) | — |
| (P2) | −0.30 | 0 (0/5) | — |
|  | 0.89 | 20 (1/5) | 11 |
|  | 2.23 | 0 (0/5) | — |
|  | 3.24 | 20 (1/5) | 10 |
|  | 4.06 | 60 (3/5) | 9 |
|  | 5.45 | 20 (1/5) | 9 |
| YF17D | 0 | 20 (1/5) | 9 |
| (ATCC) | 0 | 60 (3/5) | 10.3 |
|  | 0.9 | 100 (5/5) | 9.2 |
|  | 0.98 | 100 (5/5) | 8.2 |
|  | 2.78 | 100 (5/5) | 8 |
| Sham | N/A | 0 (0/3) | — |

[1]Actual dose delivered intracerebrally (IC) assumed to be 20 μl for back titration calculations shown.

TABLE 4

Neurovirulence of ChimeriVax ™-WN 01 site-directed mutagenesis variants at E protein residues 107, 138, 176, and 280 tested in adult mice[1]

| Virus (Vero Passage) | Target Dose ($log_{10}$ PFU) | Back Titration Dose ($log_{10}$ PFU) | % Mortality (no. dead/no. tested) | AST |
|---|---|---|---|---|
| YF/WN wt | 4 | 4.87 | 100 (5/5) | 8.6 |
| (P3) | 5 | 6.09 | 60 (3/5) | 9 |
| YF/WN$_{107}$F | 4 | 4.22 | 0 (0/5) | — |
| (P2) | 4 | 4.42 | 0 (0/8) | — |
|  | 5 | 4.99 | 0 (0/5) | — |
| YF/WN$_{138}$K | 4 | 4.26 | 60 (3/5) | 10.33 |
| (P3) | 4 | 4.41 | 63 (5/8) | 11.4 |
|  | 5 | 5.48 | 60 (3/5) | 9.33 |
| YF/WN$_{176}$V | 4 | 4.42 | 80 (4/5) | 12.5 |
| (P3) | 5 | 5.54 | 80 (4/5) | 11 |
| YF/WN$_{280}$M | 4 | 4.14 | 40 (2/5) | 9 |
| (P3) | 4 | 4.55 | 89 (7/8) | 11.86 |
|  | 5 | 5.14 | 0 (0/5) | — |
| YF/$_{107}$F$_{138}$K$_{280}$M | 4 | 3.70 | 0 (0/5) | — |
| (P2) | 5 | 4.81 | 0 (0/5) | — |
| YF/$_{107}$F$_{138}$K$_{176}$V$_{280}$M | 4 | 4.13 | 0 (0/5) | — |
| (P3) | 5 | 5.10 | 20 (1/5) | 7 |
| YF-VAX | 3 | 2.77 | 100 (5/5) | 9 |
| WN NY99 | 4 | 3.90 | 100 (5/5) | 5 |

[1]Mice inoculated IC were Taconic ICR 3–4 week old females. P2 and P3 indicate second and third generation virus passage on Vero cells, respectively.

TABLE 5

Neurovirulence of ChimeriVax ™-WN 01 site-directed mutagenesis variants at E protein residues 316 and 440 tested in adult mice[1]

| Virus IC (Vero passage) | Back Titration Dose ($log_{10}$ PFU) | % Mortality (no. dead/no. tested) | AST |
|---|---|---|---|
| YF/WN wt | 4.11 | 83 (10/12) | 9.2 |
| (P3) | 4.74 | 60 (3/5) | 10.33 |
|  | 4.83 | 100 (8/8) | 10.63 |
| YF/WN$_{316}$V | 4.09 | 25 (3/12) | 12.33 |
| (P3) | 4.67 | 38 (3/8) | 10.67 |
|  | 4.57 | 38 (9/24) | 11.22 |
| YF/WN$_{440}$R | 4.17 | 83 (10/12) | 9.22 |
| (P3) | 4.60 | 38 (3/8) | 10.33 |
|  | 4.35 | 56 (14/25) | 11.21 |
| YF/WN$_{316}$V$_{440}$R | 3.9 | 17 (2/12) | 16.5 |
| (P3) | 4.12 | 40 (2/5) | 13 |
|  | 3.71 | 36 (9/25) | 12 |

[1]Mice inoculated IC were Taconic ICR 3–4 week old females. Results of three independent experiments are shown.

TABLE 6

Neurovirulence of ChimeriVax ™-WN 02 (YF/WN$_{107}$F$_{316}$V$_{440}$R) for adult mice relative to YF/WN wt[1]

| Virus IC (Vero passage) | Back Titration Dose ($log_{10}$ PFU) | % Mortality (no. dead/no. tested) | AST |
|---|---|---|---|
| YF/WN wt (P2) | 3.62 | 42 (5/12) | 9.4 |
| YF/WN$_{107}$F$_{316}$V$_{440}$R (P4) | 5.54 | 0 (0/12) | — |
| YF/WN$_{107}$F$_{316}$V$_{440}$R (P4) | 3.72 | 0 (0/12) | — |

[1]Mice inoculated IC were Taconic ICR strain 3–4 week old females.

TABLE 7

Reciprocal neutralizing antibody titers (PRNT$_{50}$) against YF/WN wt virus. Rhesus monkeys were inoculated by the subcutaneous route with YF 17D or YF/WN vaccine candidates as specified.

| Monkey | Vaccine | Dose Log$_{10}$ PFU | Day postimmunization (dpi) | | | Day postchallenge (dpc) | |
|---|---|---|---|---|---|---|---|
| | | | 14 dpi | 30 dpi | 63 dpi | 15 dpc | 31–34 dpc |
| M017 | YF 17D | 4.49 | NT | NT | <40 | —[c] | — |
| BI01 | YF 17D | 4.49 | NT | NT | <40 | >640 | NT |
| R286 | YF 17D | 4.49 | NT | NT | <40 | — | — |
| T081 | YF 17D | 4.49 | NT | NT | <40 | >640 | NT |
| N313 | YF/WN$_{107}$F (P2) | 4.19 | 160 | >640 | >640 | 2560 | 5120 |
| P367 | YF/WN$_{107}$F (P2) | 4.19 | <40 | 640 | 640 | 5120 | 2560 |
| T087 | YF/WN$_{107}$F (P2) | 4.19 | <40 | 640 | >640 | 2560 | 1280 |
| AE81 | YF/WN$_{107}$F (P2) | 4.19 | <40 | >640 | 160 | >10240 | >20480 |
| GMT[a] | | | 57 | 640 | 453 | 4305 | 4305 |
| R918 | YF/WN$_{316}$V$_{440}$R (P3) | 4.0 | <40 | 320 | >640 | >1280 | 2560 |
| N577 | YF/WN$_{316}$V$_{440}$R (P3) | 4.0 | <40 | >160 | 320 | >1280 | 2560 |
| M233 | YF/WN$_{316}$V$_{440}$R (P3) | 4.0 | <40 | >160 | 320 | 640 | 1280 |
| T757 | YF/WN$_{316}$V$_{440}$R (P3) | 4.0 | <40 | 40 | >640 | >1280 | >5120 |
| GMT | | | 40 | 135 | 453 | 1076 | 2560 |
| J729 | YF/WN$_{FVR}$ (P4) | 3.92 | <40 | 320 | 80 | >5120 | >5120 |
| T445 | YF/WN$_{FVR}$ (P4) | 3.92 | 80 | 640 | 160 | 640 | >5120 |
| T086 | YF/WN$_{FVR}$ (P4) | 3.92 | 160 | >320 | >640 | 1280 | >5120 |
| T491 | YF/WN$_{FVR}$ (P4) | 3.92 | 80 | 320 | 160 | 2560 | >5120 |
| GMT | | | 80 | 381 | 190 | 1280 | 5120 |

[a]GMT, geometric mean titer; where the endpoint was not determined, the assay limit titer was used in the calculation (e.g., >640 taken as 640 and <40 taken as 40);
[b]NT = not tested;
[c]animal was euthanized after developing West Nile infection associated symptoms.

TABLE 8

Viremia (log$_{10}$ pfu) post vaccination; rhesus monkeys were inoculated by the subcutaneous route with YF 17D or YF/WN vaccine candidates as specified.

| Monkey | Vaccine (passage level) | Dose Log$_{10}$ PFU | Days post inoculation* | | | | | | | | | | Mean peak titer ± SD | Mean duration (days) |
|---|---|---|---|---|---|---|---|---|---|---|---|---|---|---|
| | | | 1 | 2 | 3 | 4 | 5 | 6 | 7 | 8 | 9 | 10 | | |
| M017 | YF 17D | 4.49 | 0 | 1.0[a] | 2.1 | 2.9 | 2.4 | 0 | 0 | 0 | 0 | 0 | 2.4 ± 0.5 | 3.5 |
| BI01 | YF 17D | 4.49 | 0 | 1.6 | 2.0 | 1.9 | 0 | 0 | 0 | 0 | 0 | 0 | | |
| R286 | YF 17D | 4.49 | 0 | 1.8 | 2.8 | 2.6 | 0 | 0 | 0 | 0 | 0 | 0 | | |
| T081 | YF 17D | 4.49 | 1.3 | 1.0 | 1.5 | 2.0 | 0 | 0 | 0 | 0 | 0 | 0 | | |
| N313 | YF/WN$_{107}$F (P2) | 4.19 | 1.6 | 2.0 | 1.0 | 1.3 | 1.0 | 0 | 0 | 0 | 0 | 0 | 2.2 ± 0.2 | 5 |
| P367 | YF/WN$_{107}$F (P2) | 4.19 | 0 | 1.7 | 1.6 | 1.8 | 2.3 | 1.6 | 0 | 0 | 1.3 | 0 | | |
| T087 | YF/WN$_{107}$F (P2) | 4.19 | 2.3 | 2.3 | 1.3 | 1.3 | 0 | 0 | 0 | 0 | 0 | 0 | | |
| AE81 | YF/WN$_{107}$F (P2) | 4.19 | 2.3 | 2.1 | 1.6 | 1.3 | 0 | 0 | 0 | 1.0 | 0 | 0 | | |
| R918 | YF/WN$_{316}$V$_{440}$R (P3) | 4.0 | 0 | 2.0 | 1.5 | 1.7 | 0 | 0 | 0 | 0 | 0 | 0 | 1.8 ± 0.2 | 3.5 |
| N577 | YF/WN$_{316}$V$_{440}$R (P3) | 4.0 | 1.0 | 1.9 | 1.5 | 1.0 | 0 | 1.0 | 0 | 0 | 0 | 0 | | |
| M233 | YF/WN$_{316}$V$_{440}$R (P3) | 4.0 | 0 | 0 | 1.0 | 1.0 | 0 | 0 | 0 | 1.0 | 1.6 | 1.8 | | |
| T757 | YF/WN$_{316}$V$_{440}$R (P3) | 4.0 | 0 | 0 | 0 | 1.6 | 0 | 0 | 0 | 0 | 0 | 0 | | |
| J729 | YF/WN$_{FVR}$ (P4) | 3.92 | 1.0 | 0 | 0 | 1.0 | 1.3 | 1.0 | 0 | 1.0 | 0 | 1.0 | 1.4 ± 0.2 | 4.5 |
| T445 | YF/WN$_{FVR}$ (P4) | 3.92 | 1.0 | 1.6 | 1.5 | 0 | 0 | 1.0 | 0 | 0 | 0 | 1.0 | | |
| T086 | YF/WN$_{FVR}$ (P4) | 3.92 | 1.0 | 0 | 1.3 | 1.3 | 0 | 0 | 0 | 0 | 0 | 0 | | |
| T491 | YF/WN$_{FVR}$ (P4) | 3.92 | 0 | 1.5 | 0 | 1.0 | 0 | 1.0 | 0 | 1.0 | 0 | 0 | | |

*No virus was detected in the assay at day 0 (pre-inoculation)
[a]Assay lower limit

What is claimed is:

1. A nucleic acid molecule comprising sequences encoding the pre-membrane and envelope proteins of a West Nile virus and the capsid and non-structural proteins of a Yellow Fever virus, wherein said envelope protein comprises attenuating amino acid substitutions in position 316 and position 440, or the complement of said nucleic acid molecule.

2. The nucleic acid molecule of claim 1, wherein the sequence encoded by said nucleic acid molecule further comprises an amino acid substitution in amino acid position 107.

3. The nucleic acid molecule of claim 2, wherein said amino acid substitution at position 107 is leucine to phenylalanine, or a conservative amino acid of phenylalanine.

4. The nucleic acid molecule of claim 1, wherein said amino acid substitution at position 316 is alanine to valine, or a conservative amino acid of valine.

5. The nucleic acid molecule of claim 1, wherein said amino acid substitution at position 440 is lysine to arginine, or a conservative amino acid of arginine.

6. A chimeric flavivirus encoded by the nucleic acid molecule of claim 1.

7. A method of inducing an immune response to West Nile virus in a subject, said method comprising administering to the subject the chimeric flavivirus of claim 6.

8. The method of claim 7, wherein said subject is at risk of developing, but does not have, West Nile virus infection.

9. The method of claim 7, wherein said subject is infected with West Nile virus.

10. A method of making a chimeric flavivirus vaccine, comprising introducing the nucleic acid molecule of claim 1, into cells.

11. The nucleic acid molecule of claim 1, wherein said nucleic acid molecule comprises the genome of a chimeric flavivirus comprising the pre-membrane and envelope proteins of West Nile virus and the capsid and non-structural proteins of Yellow Fever virus, wherein said envelope protein comprises attenuating amino acid substitutions in position 316 and position 440.

12. The chimeric flavivirus of claim 6, wherein the envelope protein of said chimeric flavivirus further comprises an amino acid substitution in amino acid position 107.

13. The chimeric flavivirus of claim 12, wherein said amino acid substitution at position 107 is leucine to phenylalanine, or a conservative amino acid of phenylalanine.

14. The chimeric flavivirus of claim 6, wherein said amino acid substitution at position 316 is alanine to valine, or a conservative amino acid of valine.

15. The chimeric flavivirus of claim 6, wherein said amino acid substitution at position 440 is lysine to arginine, or a conservative amino acid of arginine.

16. The method of claim 7, wherein the envelope protein of said chimeric flavivirus further comprises an amino acid substitution in amino acid position 107.

17. The method of claim 16, wherein said amino acid substitution at position 107 is leucine to phenylalanine, or a conservative amino acid of phenylalanine.

18. The method of claim 7, wherein said amino acid substitution at position 316 is alanine to valine, or a conservative amino acid of valine.

19. The method of claim 7, wherein said amino acid substitution at position 440 is lysine to arginine, or a conservative amino acid of arginine.

20. The method of claim 10, wherein the envelope protein of said chimeric flavivirus further comprises an amino acid substitution in amino acid position 107.

21. The method of claim 20, wherein said amino acid substitution at position 107 is leucine to phenylalanine, or a conservative amino acid of phenylalanine.

22. The method of claim 10, wherein said amino acid substitution at position 316 is alanine to valine, or a conservative amino acid of valine.

23. The method of claim 10, wherein said amino acid substitution at position 440 is lysine to arginine, or a conservative amino acid of arginine.

24. A vaccine composition comprising the flavivirus of claim 6.

25. The vaccine composition of claim 24, wherein the envelope protein of said chimeric flavivirus further comprises an amino acid substitution in amino acid position 107.

26. The vaccine composition of claim 25, wherein said amino acid substitution at position 107 is leucine to phenylalanine, or a conservative amino acid of phenylalanine.

27. The vaccine composition of claim 24, wherein said amino acid substitution at position 316 is alanine to valine, or a conservative amino acid of valine.

28. The vaccine composition of claim 24, wherein said amino acid substitution at position 440 is lysine to arginine, or a conservative amino acid of arginine.

* * * * *

UNITED STATES PATENT AND TRADEMARK OFFICE
CERTIFICATE OF CORRECTION

| | | |
|---|---|---|
| PATENT NO. | : 7,507,415 B2 | |
| APPLICATION NO. | : 10/715868 | |
| DATED | : March 24, 2009 | |
| INVENTOR(S) | : Arroyo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 676 days.

Signed and Sealed this
Fourth Day of January, 2011

David J. Kappos
*Director of the United States Patent and Trademark Office*